United States Patent
Wickham et al.

(10) Patent No.: US 6,603,273 B1
(45) Date of Patent: Aug. 5, 2003

(54) FAST ACCELERATING FLOW GENERATOR POWER SUPPLY

(75) Inventors: Peter John Deacon Wickham, deceased, late of Five Dock (AU), Nicola Frances Wickham, legal representative; Alexander Virr, Balmain (AU)

(73) Assignee: ResMed Limited, North Ryde (AU)

(*) Notice: Subject to any disclaimer, the term of this patent is extended or adjusted under 35 U.S.C. 154(b) by 0 days.

(21) Appl. No.: 09/763,187

(22) PCT Filed: Nov. 2, 1999

(86) PCT No.: PCT/AU99/00950

§ 371 (c)(1),
(2), (4) Date: Aug. 1, 2001

(87) PCT Pub. No.: WO00/27021

PCT Pub. Date: May 11, 2000

(30) Foreign Application Priority Data

Nov. 2, 1998 (AU) .............................................. PP 6889

(51) Int. Cl.[7] .............................................. A61M 16/00
(52) U.S. Cl. .............................. 315/241 R; 128/204.23
(58) Field of Search ..................... 315/241; 128/204.23, 128/204.18, 204.21, 204.26, 204.22, 204.24

(56) References Cited

U.S. PATENT DOCUMENTS

| | | | |
|---|---|---|---|
| 4,727,297 A | 2/1988 | Wolze | 315/307 |
| 4,900,990 A | 2/1990 | Sikora | 315/241 P |
| 5,523,654 A | 6/1996 | Sikora et al. | 315/241 R |
| 6,213,119 B1 * | 4/2001 | Brydon et al. | 128/204.23 |

FOREIGN PATENT DOCUMENTS

EP          656 216        6/1995

* cited by examiner

Primary Examiner—James Clinger
(74) Attorney, Agent, or Firm—Pillsbury Winthrop LLP

(57) ABSTRACT

Methods and apparatus for the supply of non-invasive positive pressure ventilation by motor-driven blowers, and having fast acceleration between treatment pressures, are described. A blower (12) supplies treatment pressure of air or breathable gas to a patient mask (16) via a conduit (14) at a first pressure and at a second, higher pressure. The blower (12) receives its power from a power supply (22) and cascaded motor controller (20). The power supply (22) has the capacity to supply sufficient power for the first pressure to be achieved. A static capacitor (24), that is charged by the power supply (22), provides the energy to the blower (12) to achieve the second pressure, during which period the power supply (22) is effectively shut down.

6 Claims, 4 Drawing Sheets

FAST ACCELERATING FLOW GENERATOR POWER SUPPLY

FIELD OF THE INVENTION

The invention relates to flow generators for the supply of non-invasive positive pressure ventilation (NIPPV) for treating respiratory disorders, and in particular flow generator power supplies providing fast acceleration between treatment pressures.

BACKGROUND OF THE INVENTION

Acute respiratory insufficiency may be treated with devices which provide positive pressure ventilatory assistance. Sleep disordered breathing, such as Obstructive Sleep Apnea (OSA) is also treated with these devices. A typical device comprises a controllable flow generator coupled to a nasal mask and provides a supply of breathable gas to a patient in the range 4 to 30 $cmH_2O$ positive pressure. Nasal prongs, a mouth mask or full face mask may be used as alternatives to a nasal mask. A reference to a mask herein is intended to include a reference to any of these patient interface devices.

The devices can supply gas at a relatively higher pressure during the inspiratory phase of respiration (IPAP) and a relatively lower pressure or atmospheric pressure during the expiratory phase of a respiration (EPAP). In other NIPPV modes, the pressure can be made to vary in a complex manner throughout the respiratory cycle. For example, the pressure at the mask during inspiration or expiration can be varied through the period of treatment.

Two ways of varying the pressure at the mask are (a) by mechanical or pneumatic valving ('valved machines') and (b) by utilising speed control of the motor/blower to control the output pressure of the flow generator ('variable speed machines'). Valved machines are fast acting, however the valve mechanisms are complicated and expensive. Variable motor speed machines are considerably simpler, having only one moving part, namely the blower rotor. As such, these machines are cheaper to manufacture, and, in turn, cheaper to purchase.

Of particular interest is the time required for the transistion between EPAP and IPAP, this time being termed the 'transition time'. In order that treatment efficacy and patient comfort are retained, the transistion time should be short. Variable speed machines generally have a longer transition time than valved machines. Transition times in the order of 200 to 500 ms are known. In the case of acute respiratory insufficiencies such as lung disease, emphysema and cystic fibrosis, a long transition time is unsatisfactory and can jeopardise treatment. For these conditions, a transition time of approximately 50 ms is generally acceptable.

To achieve a short transition time in a variable speed machine, the flow generator must accelerate quickly. Deceleration is readily achieved with excess energy lost to a heak sink or lost mechanically. Most currently used motor/blower units are capable of achieving the necessary acceleration if they are provided with sufficient power. The primary limitation is in the power supply. The power requirement during steady state typically is 20 Watts. However, for a short transition time, the power requirement rises to approximately 200 Watts. One possible solution is to increase the size of the power supply. The problem with that solution is that is also increases the weight and cost of the device.

It is an object of the invention to solve the problem of providing a flow generator with sufficient power to enable fast acceleration without the need for a physically large, complex and expensive power supply.

SUMMARY OF THE INVENTION

Accordingly, the invention discloses a power supply for a motor speed-controlled flow generator, comprising: a power supply circuit having input terminals to receive an input power supply and having output terminals to provide an output power supply for connection to an electrical load; and energy storage means coupled to said output, the energy storage means being charged by the output supply and operable to discharge the energy stored therein when the circuit cannot provide the full amount of a demanded load.

The invention further discloses a flow generator, including a blower for the provision of an output supply of air or breathable gas at a pressure elevated above atmospheric pressure, a motor driving the blower at a controlled speed, a motor controller for controlling the motor speed and hence the output pressure of the blower, and a power supply as defined immediately above coupled by the output terminals to the motor controller, the flow generator being operable such that on a demanded increase in treatment pressure from a first level to a second level, the energy storage means provides energy for acceleration that is not otherwise available from the power supply circuit of the power supply.

The invention yet further discloses motor speed controlled positive pressure ventilation apparatus, including a flow generator as defined immediately above, having connection to an air delivery conduit connected with a patient mask. In one preferred form, the apparatus provides bi- or multi-level CPAP treatment.

The invention yet further provides a method for supplying non-invasive positive pressure ventilation to a patient's airways at a first pressure and a second, higher pressure, the method comprising the steps of:

providing a power supply with sufficient capacity to supply a variable speed motor-driven blower such that the first pressure can be achieved; and providing a further static source of energy that has the capacity to replace the power supply and supply the blower such that the second pressure can be achieved.

It is particularly preferred that the energy storage means is a static capacitor connected across the output terminals. The energy storage means also can include a switch means, such as a transistor or a thyristor or a GTO device, to controllably switch the capacitor. Yet further, the circuit of the power supply can exhibit a voltage versus current characteristic having a first approximately constant voltage region up to a first current value and a second approximately constant current region beyond that value, in which second region the voltage reduces to a zero value. The capacitor will be switched, or come into operation at approximately said first current value.

BRIEF DESCRIPTION OF THE DRAWINGS

An embodiment of the invention will now be described with reference to the accompanying drawings, in which.

DETAILED DESCRIPTION AND BEST MODE

The embodiment to be described is a bi-level CPAP machine that is one form of the general class of non-invasive positive pressure ventilation devices.

Figure 1:
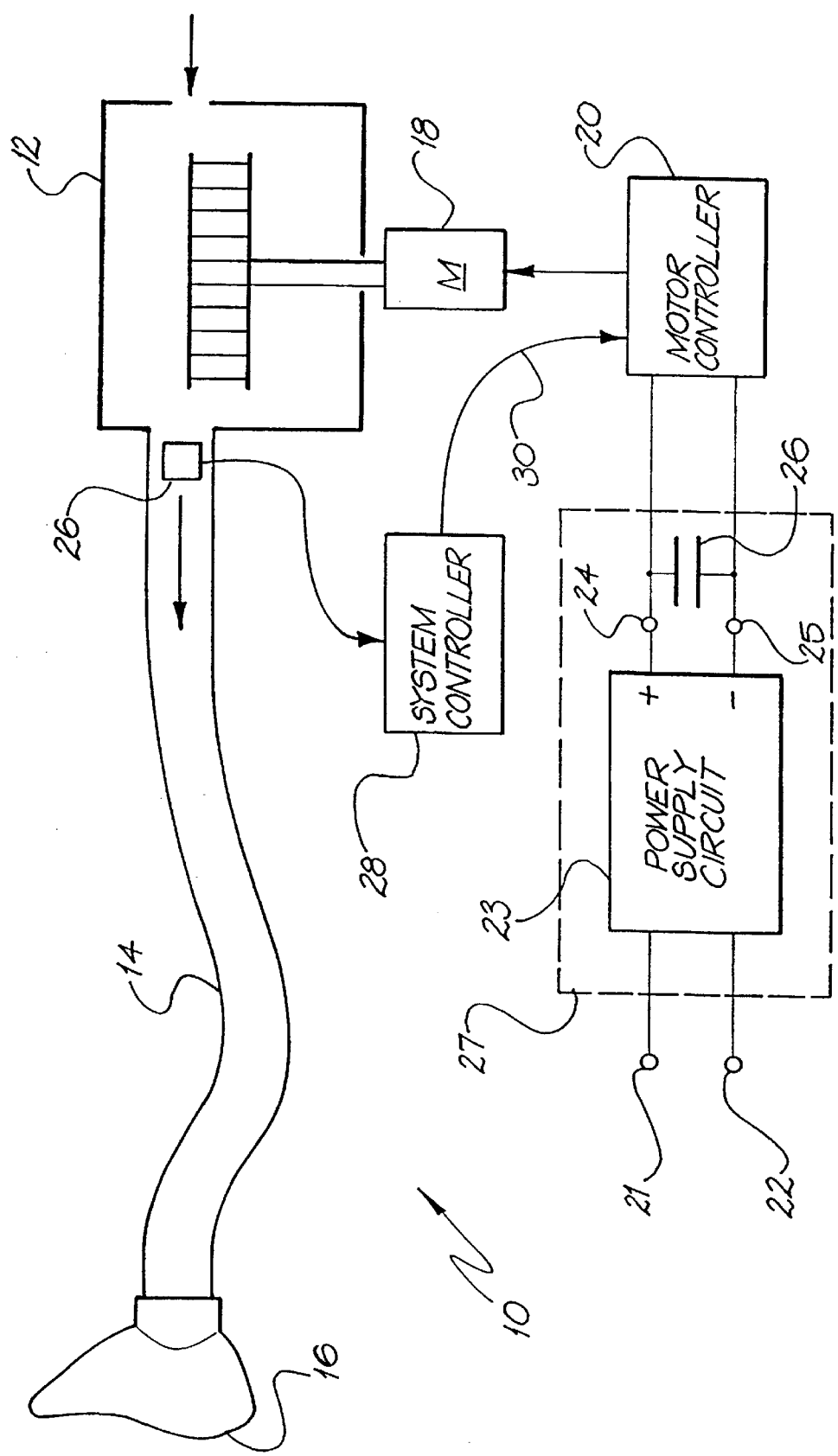
FIG. 1 shows a schematic block diagram of a bi-level CPAP machine embodying the invention.

The bi-level CPAP machine 10 shown in FIG. 1 has a blower 12 receiving a supply of air or breathable gas and providing a pressurised flow of air or gas at an outlet to a flexible conduit 14 transporting the gas to a patient mask 16. The blower 12 receives its rotational energy from an electric motor 18. The speed of the motor 18, determined by the motor controller 20, determines the blower output pressure, and thus the treatment pressure at the mask 16. A typical motor that can be used in such a machine is a six pole brushless DC permanent magnet motor.

The power supply circuit 23 receives a supply of AC mains power at the input terminals 21,22, converting it to an output DC supply on the output terminals 24,25 that is received by the motor controller 20. The motor controller 20 converts the DC supply into the necessary switched mode (pseudo-AC) supply required by the motor 18. The DC output of the power supply circuit 23 has a capacitor (or bank of capacitors) 26 connected across the output terminals 24,25, the function of which will presently be described. The circuit 23 and capacitor 26 together form the power supply 27 of the CPAP machine 10.

The gas outlet from the blower 12 to the conduit has a flow sensor 26 located in or near it providing a signal to a system controller 28 representative of patient respiratory flow. Amongst the other functions performed by the system controller, it determines the time instance of triggering between IPAP and EPAP phases and provides a controlling signal to the motor controller to effect the desired motor speed and thus the desired treatment pressure. In the present embodiment, the control signal 30 is operative on the transition between EPAP and IPAP states where fast acceleration of the motor is required.

During steady state periods of the bi-level treatment, the electrical load provided by the motor demands approximately 20 Watts of power from the power supply circuit 23, being 30 V at 0.66 A. The power supply circuit 23 is typically rated at 50 W with a maximum current of 1.6–1.8 A. On the EPAP to IPAP transition the motor 18 will demand approximately 200 Watts, equivalent to 6.6 A. During the 50 ms rise time, this additional power demand is provided by the static capacitor 26. That is, during the steady state periods the capacitor becomes fully charged, and when the power supply circuit 23 cannot meet the full instantaneous demand of the motor, supplies that stored energy to the motor. In the particular embodiment described, the energy requirement is 50 joules. At 30 V, the necessary capacitance to provide this energy is approximately 0.1 F, viz., $E=\frac{1}{2} CV^2$.

A capacitor of the order of 0.1 F is relatively compact and inexpensive in comparison with a power supply circuit 23 constructed to provide both the steady state and transient load demand. Indeed, the cost of such a circuit might increase by a factor of four and its physical size be doubled.

Figure 2:
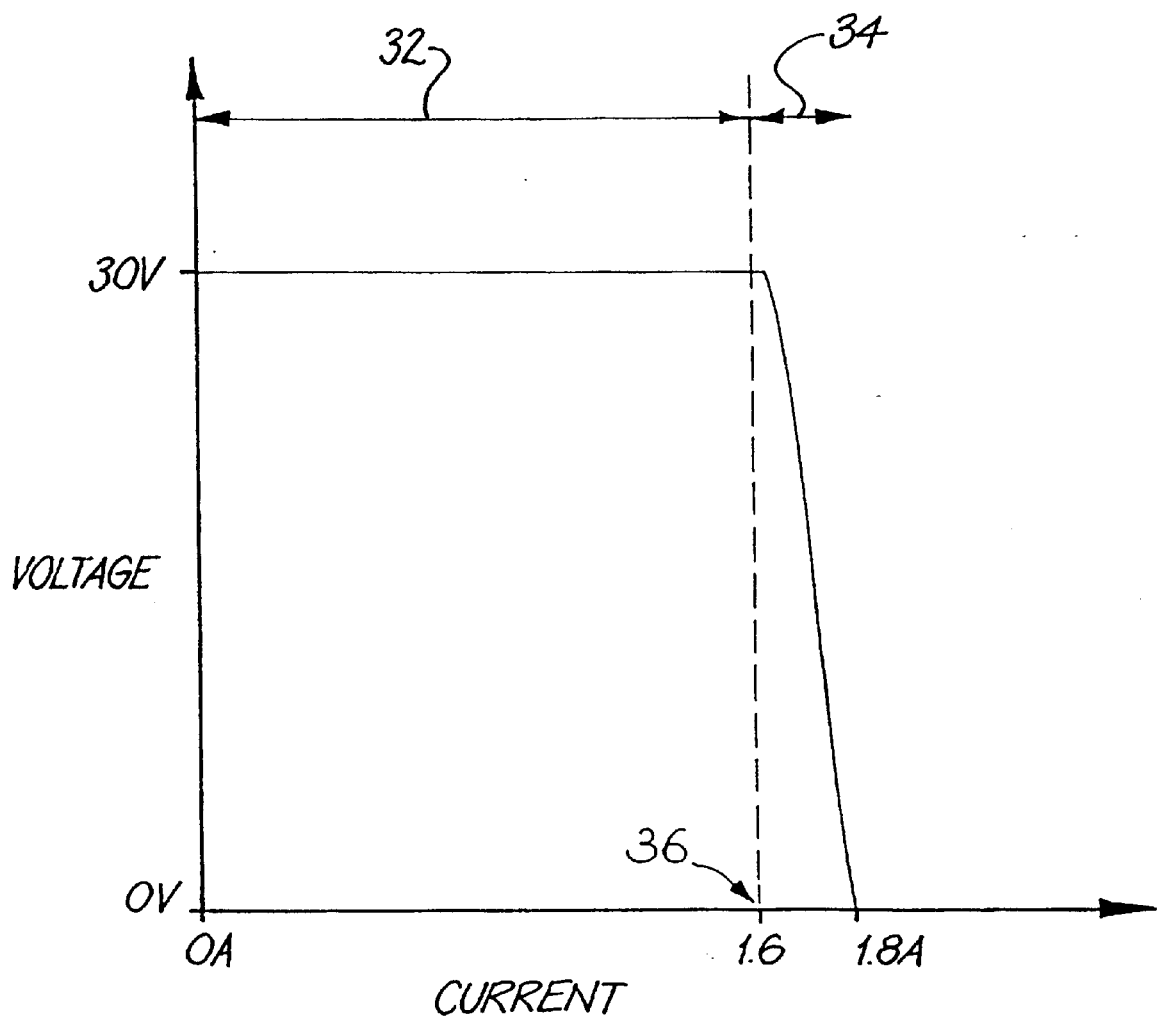
FIG. 2 shows the voltage and current characteristic of the power supply circuit.

The nature of the capacitor 26 is to supply its stored energy only if the output voltage of the power supply circuit 23 drops below the nominal (30 V) output level. In that case, it is necessary for the power supply to exhibit a characteristic as shown in FIG. 2, where there is a constant voltage region up to a current value of 1.6 A, followed by an approximate constant current region up to a maximum current value of 1.8 A, during which the voltage drops linearly to zero.

Accordingly, the power supply circuit 23 is clamped when the current level exceeds 1.8 A, and does not seek to supply the full voltage until the demanded current level decreases below 1.6 A. Were it otherwise, the energy supply from the capacitor 26 could be interrupted or become 'spiky'.

Figure 3:
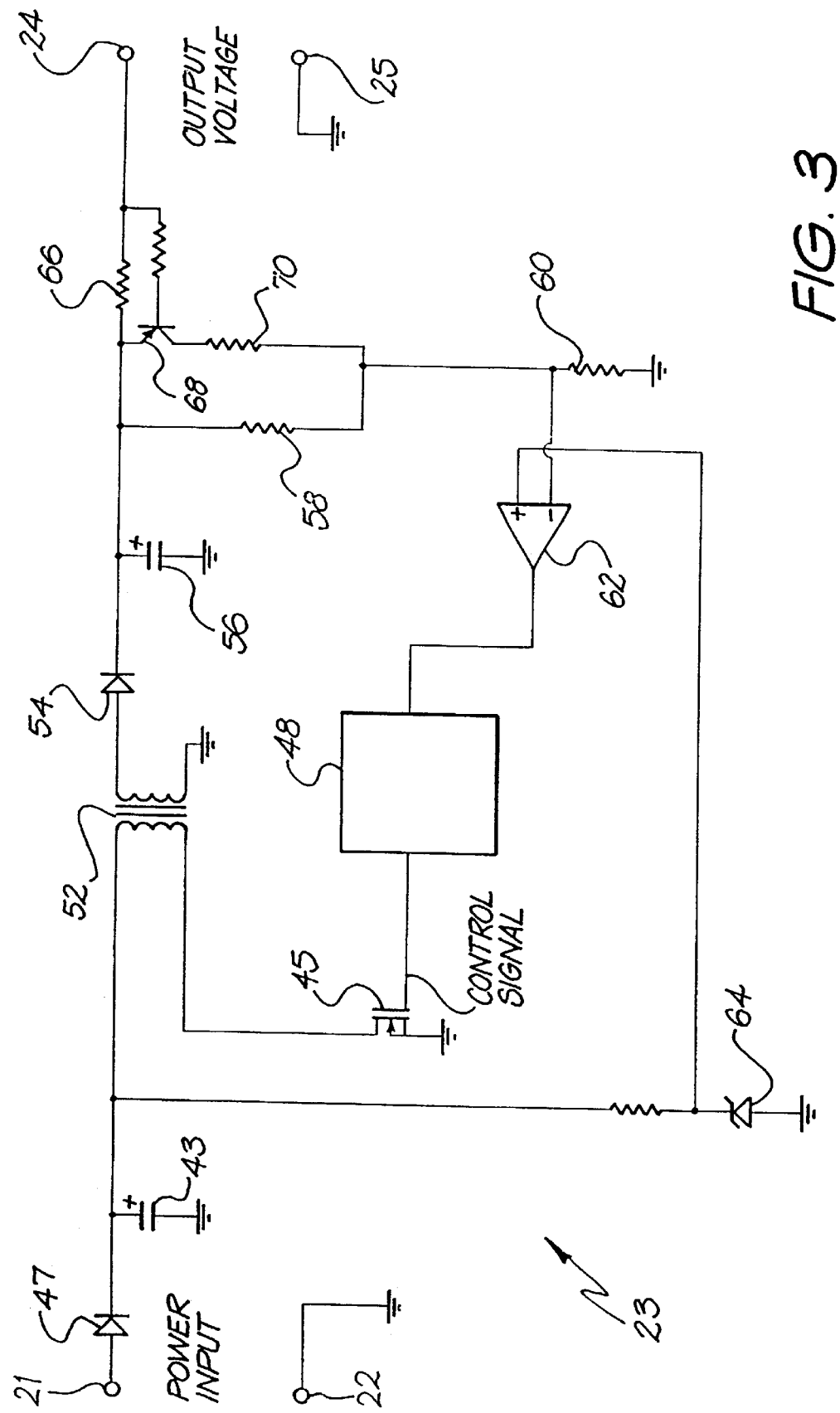
FIG. 3 shows an electrical block diagram of the power supply circuit.

FIG. 3 shows a circuit schematic of the power supply circuit 23. AC mains power is applied through the power input terminals 21,22. The AC power is rectified and filtered by a diode 47 and a capacitor 43. The high voltage appearing across the capacitor 43 is transformed to a lower regulated output voltage, available at the output terminals 24,25, by the switching operation of a power FET 45 occurs by a control signal, supplied by a pulse width controller 48 operating at a high frequency (20 to 200 kHz), hence switching the voltage across the capacitor 43 through the transformer 52. The output of the transformer 52 is rectified and filtered by a diode 54 and capacitor 56 arrangement.

The voltage across the capacitor 56 is maintained at a constant level by a voltage feedback network of two resistors 58,60, in that the operational amplifier 62 compares the voltage across the resistor 60 with a voltage reference supplied by the voltage reference diode 64. The output of the operational amplifier 62 adjusts the duty cycle of the control signal, supplied by the pulse width controller 48 to the power FET 45.

A constant voltage is maintained at the output terminals 24,25 as long as the current through the current sensing resistor 66 is low enough such that the transistor 68 is not turned on (typically such that the voltage across the resistor 66 is less than 0.6 V). The value of the current sensing resistor 66 is selected such that the transistor 68 starts to turn on at the threshold current of 1.6 A as shown in FIG. 2, where a transition from constant voltage to constant current is required. For output current levels higher than the threshold current, transistor 68 is turned on, shunting the voltage feedback network resistors 58 and 60 with another resistor 70 which causes the output voltage at the terminals 50 and 51 to be regulated at a lower level.

The power supply circuit 23 supplies an output voltage at the output terminals 24,25 which is regulated at a constant level for all currents below the threshold current 36 set by the current sensing resistor 66, and reduced to maintain a maximum current at threshold current 36. In this way the power supply circuit 23 is clamped. As described above, this threshold current 36 is reached when the motor 18 is accelerating from the EPAP phase to IPAP phase.

Figure 4A:
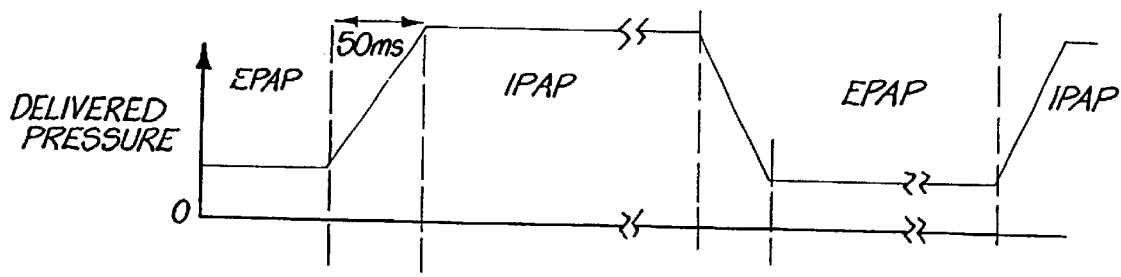
FIGS. 4a–4d show plots of machine characteristics during acceleration and deceleration.
Figure 4B:
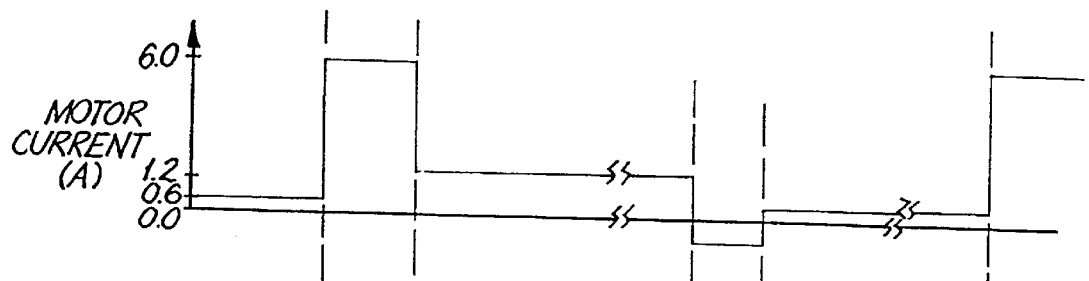
Figure 4C:
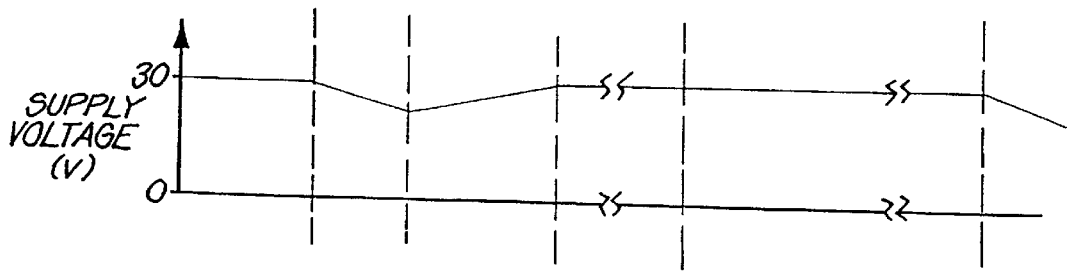
Figure 4D:
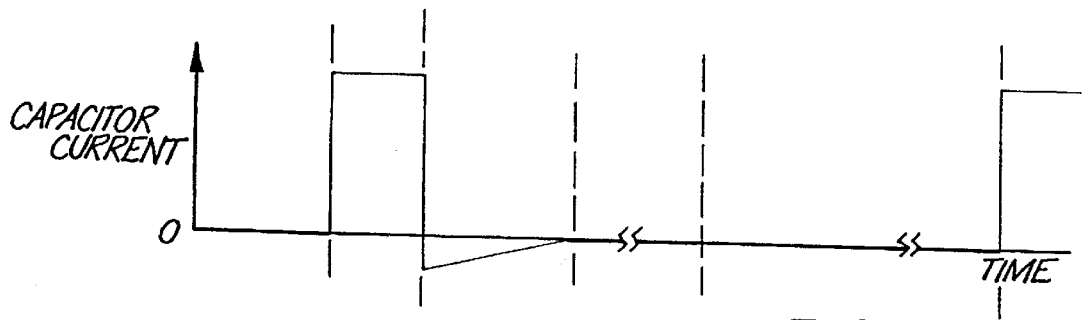

FIG. 4a shows a first transition between an EPAP phase and an IPAP phase, with the 50 ms motor acceleration period, shown in exaggerated form for the purpose of clarity. As shown in FIG. 4b, on the triggered transition between EPAP and IPAP phases the demanded motor current increases to 6 A. The power supply circuit 23 will be clamped once the current demand exceeds 1.6 A and the balance of the demanded current is provided by the capacitor 26. As the capacitor supplies energy, its terminal voltage will decrease as shown in FIG. 4c, generally following the characteristic of FIG. 2. Once the motor reaches the IPAP level, the motor current decreases to a normal level of 1.2 A, which is supplied by the power supply 22 again, meaning that there is inrush (negative) charging current flowing to the capacitor 24 as recharging occurs until such time as the capacitor is fully recharged. In the same recharging period the supply voltage at the output terminals 24,25 increases to the nominal 30 V level. Voltage regulation is not of concern in the present embodiment as the motor controller 22 controls the motor 18 on the basis of demanded current and the frequency of the switched pseudo AC supply provided thereto.

The transition from the IPAP phase to the EPAP phase is a form of mechanical braking, wherein the motor current drops to a zero value and the motor and turbine in combination decelerate to a speed corresponding to the desired EPAP value in a sufficiently short time.

Although the invention has been described with reference to a preferred embodiment, it will be appreciated by those skilled in the art that the invention may be embodied in many other forms.

For example, a static capacitor can be additionally controlled by a semiconductor switch, such as a power transistor, FET or GTO device.

What is claimed is:

1. A power supply for a motor speed-controlled flow generator, comprising:

a power supply circuit having input terminals to receive an input power supply and having output terminals to provide an output power supply for connection to an electrical load; and a static capacitor connected across to said output terminals, the static capacitor being charged by the output supply and operable to discharge the energy stored therein when the circuit cannot provide the full amount of a demanded load, wherein the power supply circuit exhibits a voltage versus current characteristic having a first approximately constant voltage region up to a first current value, and a second approximately constant current region beyond the first current value, in which second region the voltage decreases to a zero value, the capacitor being switched or coming into operation at approximately said first current value.

2. A power supply as claimed in claim 1, further comprising a switch to controllably switch the capacitor to be electrically connected to the output terminals.

3. A flow generator for the supply of non-invasive positive pressure ventilation, comprising:

a blower to provide an output supply of air or breathable gas at a pressure elevated above atmospheric pressure;

a motor to drive the blower at a controlled speed;

a motor controller to control the motor speed and hence the output pressure of the blower; and a power supply having a power supply circuit to receive an input power supply and to provide an output to said motor, and a static capacitor connected across the output and being charged by said output;

wherein the flow generator is operable such that, on a demanded increase in treatment pressure from a first blower pressure level to a second higher blower pressure level, the static capacitor provides energy to the motor for blower acceleration that is not otherwise available from the power supply circuit, and wherein the power supply circuit exhibits a voltage versus current characteristic having a first approximately constant voltage region up to a first current value and a second approximately constant current region beyond the first current value, in which second region the voltage decreases to a zero value, the capacitor being switched or coming into operation at approximately said first current value.

4. A flow generator as claimed in claim 3, further comprising a switch to controllably switch the capacitor to the output terminals of the power supply.

5. A motor speed-controlled non-invasive positive pressure ventilation apparatus comprising:

a flow generator as claimed in claim 3; and an air delivery circuit.

6. An apparatus as claimed in claim 5, wherein said air delivery circuit includes a conduit connected to the blower to receive the output supply, and a mask to provide pressurised air or breathable gas to a patient's airways.

* * * * *